United States Patent
Balteau

(10) Patent No.: US 8,430,128 B2
(45) Date of Patent: Apr. 30, 2013

(54) INTERLOCKING TUBING CLAMPS

(75) Inventor: Patrick Balteau, Evelette (BE)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 701 days.

(21) Appl. No.: 12/615,705

(22) Filed: Nov. 10, 2009

(65) Prior Publication Data

US 2011/0112489 A1    May 12, 2011

(51) Int. Cl.
*F16K 35/14*    (2006.01)

(52) U.S. Cl.
USPC .............................. 137/637.1; 251/10; 251/90

(58) Field of Classification Search .................. 137/637, 137/637.1; 251/9, 10, 90; 604/250
See application file for complete search history.

(56) References Cited

U.S. PATENT DOCUMENTS

| | | | |
|---|---|---|---|
| 5,203,056 A | 4/1993 | Funk et al. | |
| 5,662,144 A | 9/1997 | Lo et al. | |
| 6,161,812 A | 12/2000 | Guala et al. | |
| 6,592,558 B2 * | 7/2003 | Quah | 604/250 |
| 6,837,787 B2 * | 1/2005 | Crook | 454/292 |
| 6,913,056 B2 | 7/2005 | Landherr et al. | |
| 7,226,649 B2 | 6/2007 | Shang et al. | |
| 7,234,677 B2 * | 6/2007 | Zerfas | 251/10 |
| 2003/0143352 A1 | 7/2003 | Yang et al. | |

FOREIGN PATENT DOCUMENTS

| | | |
|---|---|---|
| EP | 0 995 462 | 4/2000 |
| EP | 1 106 191 | 6/2001 |
| EP | 1 905 478 | 4/2008 |
| EP | 2 204 216 | 7/2010 |
| WO | 01/24870 | 4/2001 |

OTHER PUBLICATIONS

Notification of Transmittal of The International Preliminary Report on Patentability for International Application No. PCT/US2010/055982 mailed on Feb. 10, 2012.
International Search Report and Written Opinion for International Application No. PCT/US2010/055982 mailed on Mar. 23, 2011.

\* cited by examiner

*Primary Examiner* — John K Fristoe, Jr.
*Assistant Examiner* — Daniel Edelbrock
(74) *Attorney, Agent, or Firm* — K&L Gates LLP

(57) ABSTRACT

A tube clamp includes (i) a tube holding portion; (ii) a first arm extending from a first end of the tube holding portion; (iii) a second arm extending from a second end of the tube holding portion, the second armed curved so that a first catch located at a distal end of the second arm can be snap-fitted to the first arm to occlude a first tube extending through the tube holding portion; and (iv) wherein the first arm includes a locking feature configured such that when a second tube clamp is mated with the tube clamp, the locking feature interacts with a second catch of the second tube clamp so that the second tube clamp is prevented from occluding a second tube.

6 Claims, 6 Drawing Sheets

INTERLOCKING TUBING CLAMPS

BACKGROUND

The present disclosure relates generally to medical fluid handling and in particular to the packaging and sterilization of medical fluid bags or containers.

It is known to package a sterile medical fluid, such as dialysis fluid, in medical fluid bags. The bags in many instances are provided with tubing preconnected to the bags. This tubing needs to be sterilized. One method of sterilization is steam sterilization. Steam sterilization is advantageous over other forms of sterilization, such as ethylene oxide ("EtO") sterilization, which requires the application of a vaporized chemical, and gamma radiation, which can leave an odor and/or discolor the sterilized item.

One requirement for steam sterilization however is that the surface to be sterilized must be adequately contacted by the steam. Failure to do so will result in an improperly sterilized item.

The bag tubing set is often provided with one or more external clamps, such as a Roberts™ clamp. For various reasons, the external clamps may become partially or fully closed or clamped, for example, during shipping or during the sterilization process itself. It is desirable to pre-attach the external clamps prior to shipping and sterilization, creating the need for an apparatus and method to prevent the external clamps from becoming inadvertently locked or closed prior to sterilization.

SUMMARY

The present disclosure sets forth an apparatus and method for preventing the inadvertent closure or clamping of an external clamp provided on a tubing set. The apparatus includes a clamp that is configured to mate with a second like clamp in such a way that the clamps interlock and prevent each other from being closed or clamped inadvertently until the matched clamp pair is pulled apart manually. The method includes positioning each of two manual clamps over a separate tube, so as to face opposite directions, and then sliding the clamps over their respective tubes towards each other until the oppositely facing clamps snap-fit together in an interlocking relationship. Doing so also routes the respective tubes together desireably at the interlocked clamps.

It is contemplated to structure the external clamps in different ways to enable mated pairs of clamps to be interlocked together. In each case, the clamps are generally U-shaped, wherein the rounded base of the U defines a tube holding aperture. The inner wall of the rounded base of the tube holding portion transitions to a pair of clamping jaws. The clamping jaws occlude the tubing when the clamp is closed.

First and second arms extend outwardly from the rounded base of the U or tube holding portion. A first arm is substantially straight and includes ratcheted ribs on its outer surface for the user to grip when closing the clamp. A second arm is rounded or curved and bends so that it terminates at a catch located near a distal end of the first arm. To close the clamp, the user pinches or compresses the ribbed arm towards the circular arm, such that the distal end of the straight arm engages and slides past the catch at the distal end of the curved arm. Doing so bends the curved arm outwardly to allow the distal end of the ribbed arm to slide past the catch, at which point the catch and distal end of the curved arm snap back to an unstressed and locked position. At such point, the distal end of the ribbed arm is trapped below the catch. The pinching of the first and second arms also pinches together the clamping jaws, which occludes the tube. When the user wishes to open the tube, the user pushes the catch away from the distal end of the straight arm, allowing the inherent springiness of the clamp and the compressed tube to open the clamp.

The clamps of the present disclosure can be configured to be interlocked in a non-closeable position with another like clamp in at least three different ways. In a first way, a bump or protrusion is added to the first arm at the beginning of the ribs. The bump of a fist one of the clamps engages the catch of a second one of the clamps. Likewise the catch of the second clamp engages the bump or protrusion of the first clamp. In this manner the clamps are prevented from being moved towards or away from each other in a direction coincident with the axis of the tubing running through the clamps. Because the clamps are not readily able to be pulled apart from each other, the clamps are not readily able to become individualized, in which case the clamps could be compressed and closed, occluding the tubing. Also, first arms of each of the interlocked clamps prevent the second arms of the respective mated clamps from closing and locking to the end of the respective first arms.

The bump or protrusion in one embodiment thickens the ribbed arm of the clamp, such that the curved arms of the mated clamps are locked at a position such that the clamps are more spread apart than if the ribbed arms had not been thickened. The additional spreading apart of the clamp arms also additionally spreads apart the clamping jaws, such that the tubes reside even more freely within the clamps.

In a second embodiment, the bumps of the first embodiment are replaced with ramps. Here, the ribbed arm of each clamp is ramped beginning at the distal end or tip of the ribbed arm and ramps upwards as the ribbed arm extends towards its proximal end adjacent the rounded section of the U or tube holding portion of the clamp. At a desired point the ramp ends and steps down to the unramped thickness of the ribbed arm. The ramped clamps operate to restrain axial and compressive movement when mated in the same manner as the bumps or protrusions of first embodiment. The ramps indeed can be thought of as a modified bump or protrusion.

In a third embodiment, the bumps or ramps are replaced with recesses. The ends and catches of the second, curved arms snap into the recesses of the mated clamps. Axial and compressive movement is thereby prevented.

It is accordingly an advantage of the present disclosure to provide an improved medical tubing clamp.

It is another advantage of the present disclosure to provide an improved tubing sterilization apparatus.

It is a further advantage of the present disclosure to provide an improved tubing sterilization method.

Additional features and advantages are described herein, and will be apparent from the following Detailed Description and the figures.

DETAILED DESCRIPTION

Figure 1:
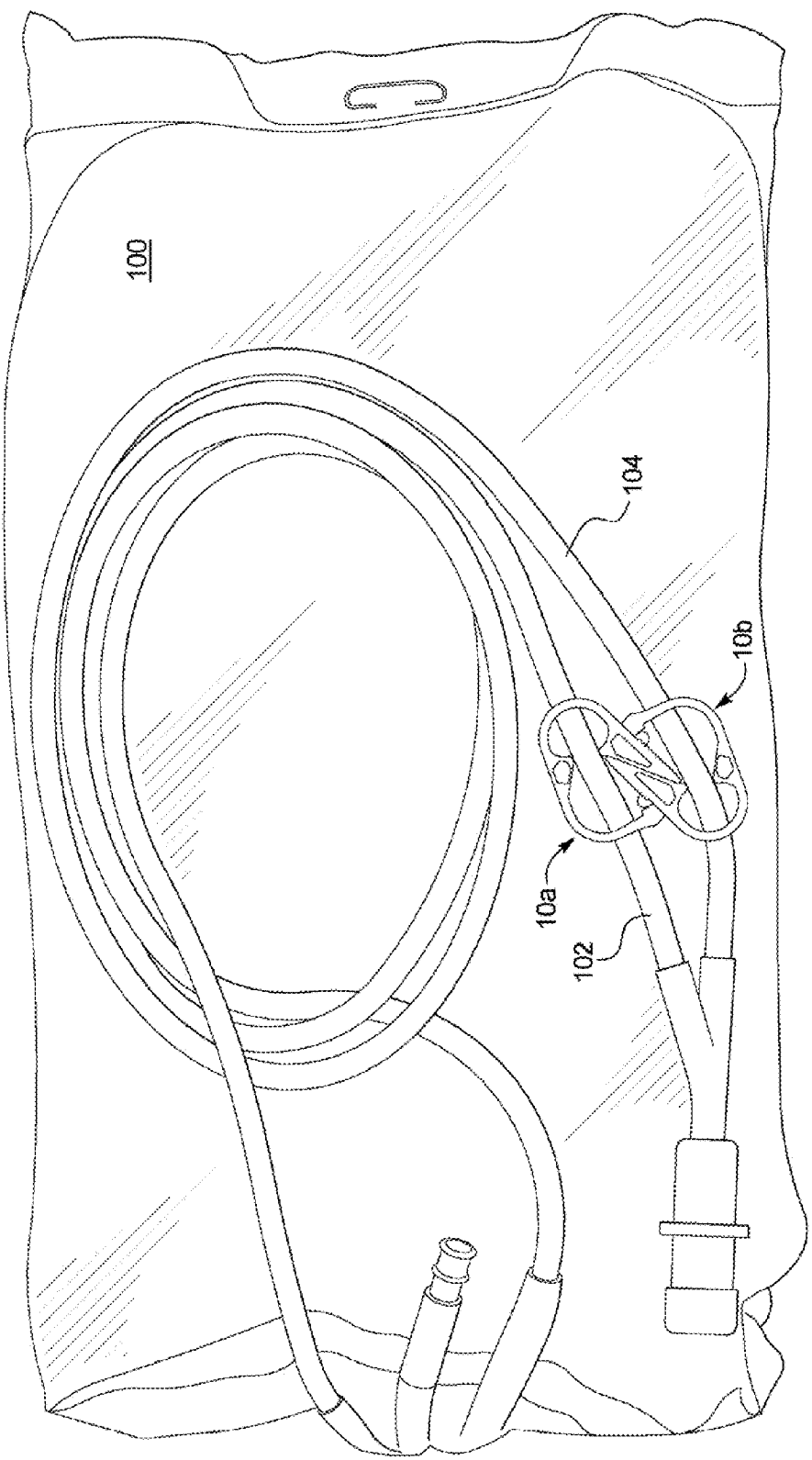
FIG. 1 is a perspective view illustrating one application for the interlocking tube clamps of the present disclosure.

One application for the interlocking tubing clamps of the present disclosure is a dual filled twin bag. One suitable twin bag is set forth in U.S. Pat. No. 6,196,991 ("the '991 patent") assigned to the assignee of the present disclosure, the entire content of which are expressly incorporated herein by reference and relied upon. As seen in FIGS. 1 and 2 of the '991 patent, each bag of the twin bag assembly communicates with a tube. The tubes are Y-d together at their distal ends to form a single outlet.

Referring now to the drawings and in particular to FIG. 1, it is desirable to equip tubes 102 and 104 of twin bag assembly 100 with first and second external clamps 10a and 10b, even before the tubes 102 and 104 and bag interiors of twin bag assembly 100 are sterilized, such as steam sterilized. To prevent clamps 10a and 10b from being collapsed prior to or during sterilization, clamps 10a and 10b of the present disclosure have been configured such that the clamps are interlocked together until pulled apart.

Figure 2A:
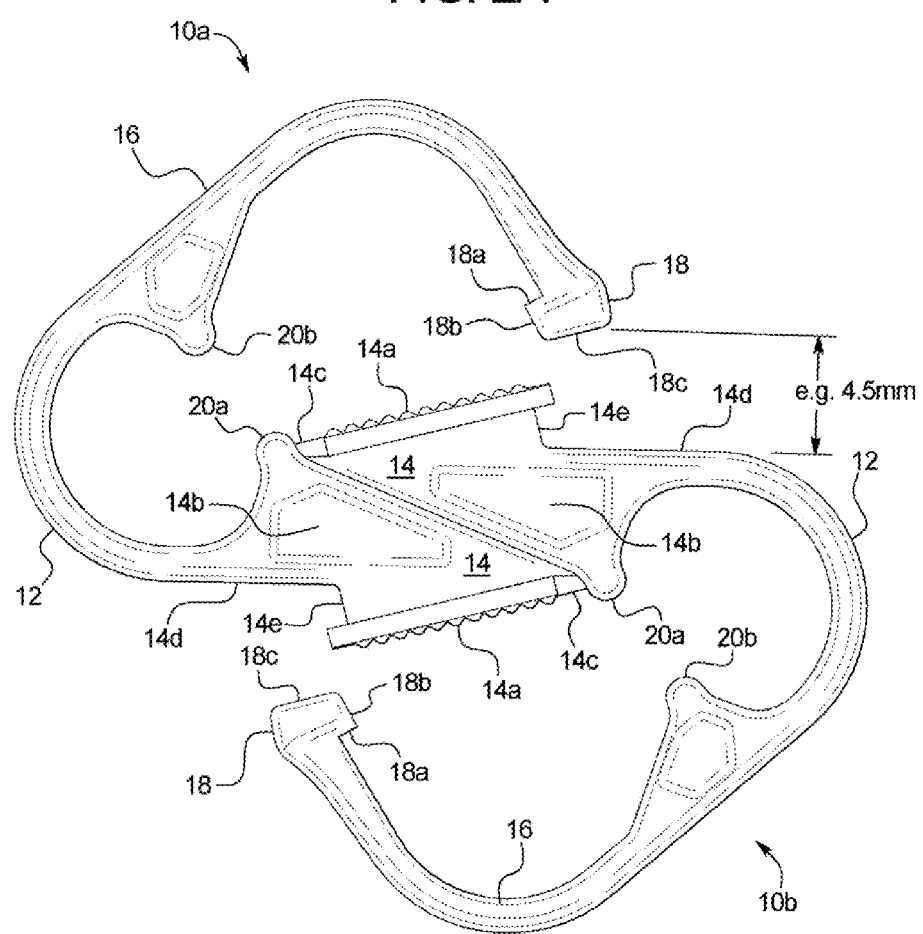
FIG. 2A is an elevation view of one embodiment of the interlocking tubing clamps of the present disclosure in a pulled apart condition.
Figure 2B:
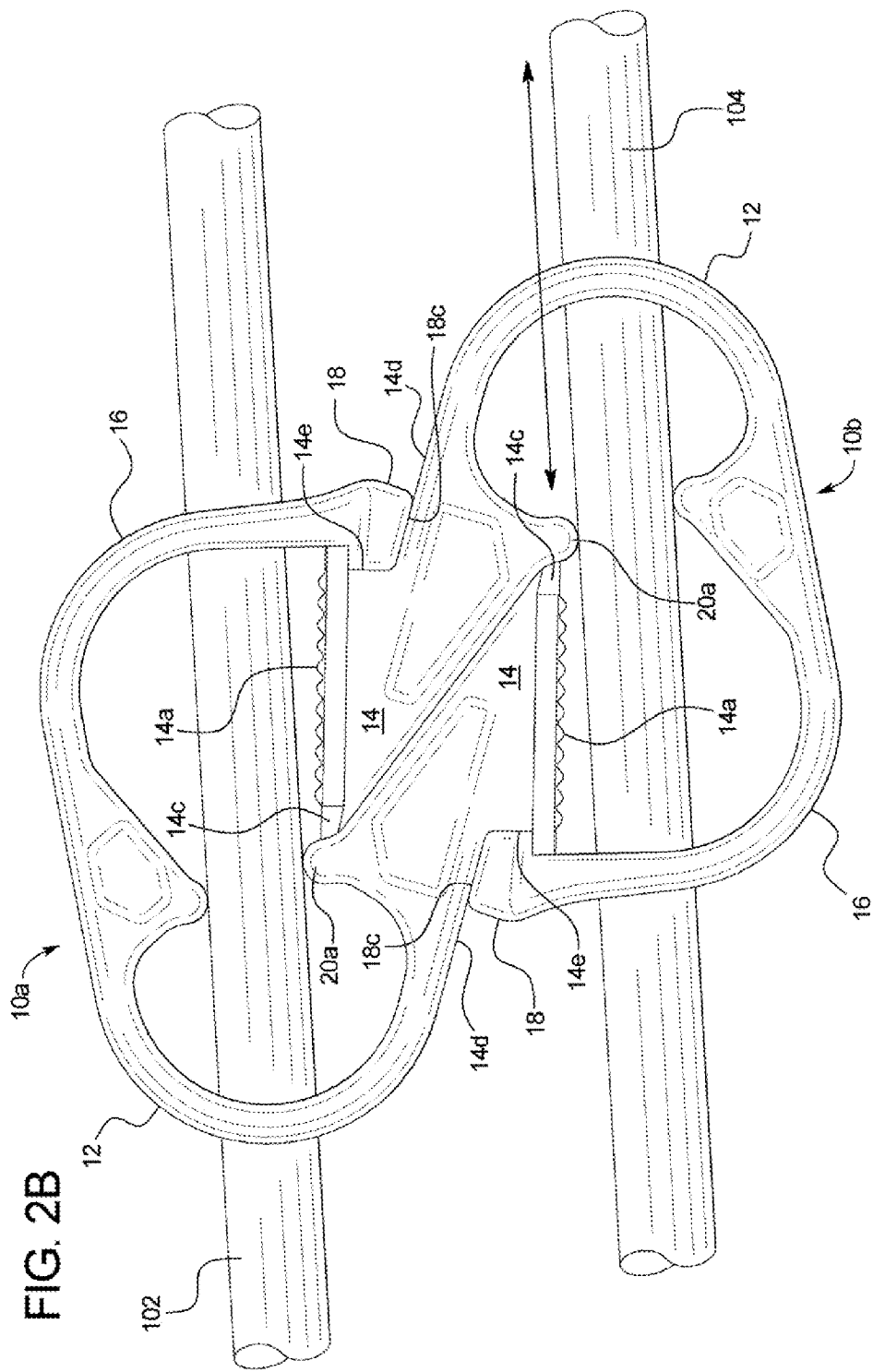
FIG. 2B is an elevation view of the embodiment of the interlocking tubing clamps of FIG. 2A in an imbricated or interlocked condition.
Figure 3:
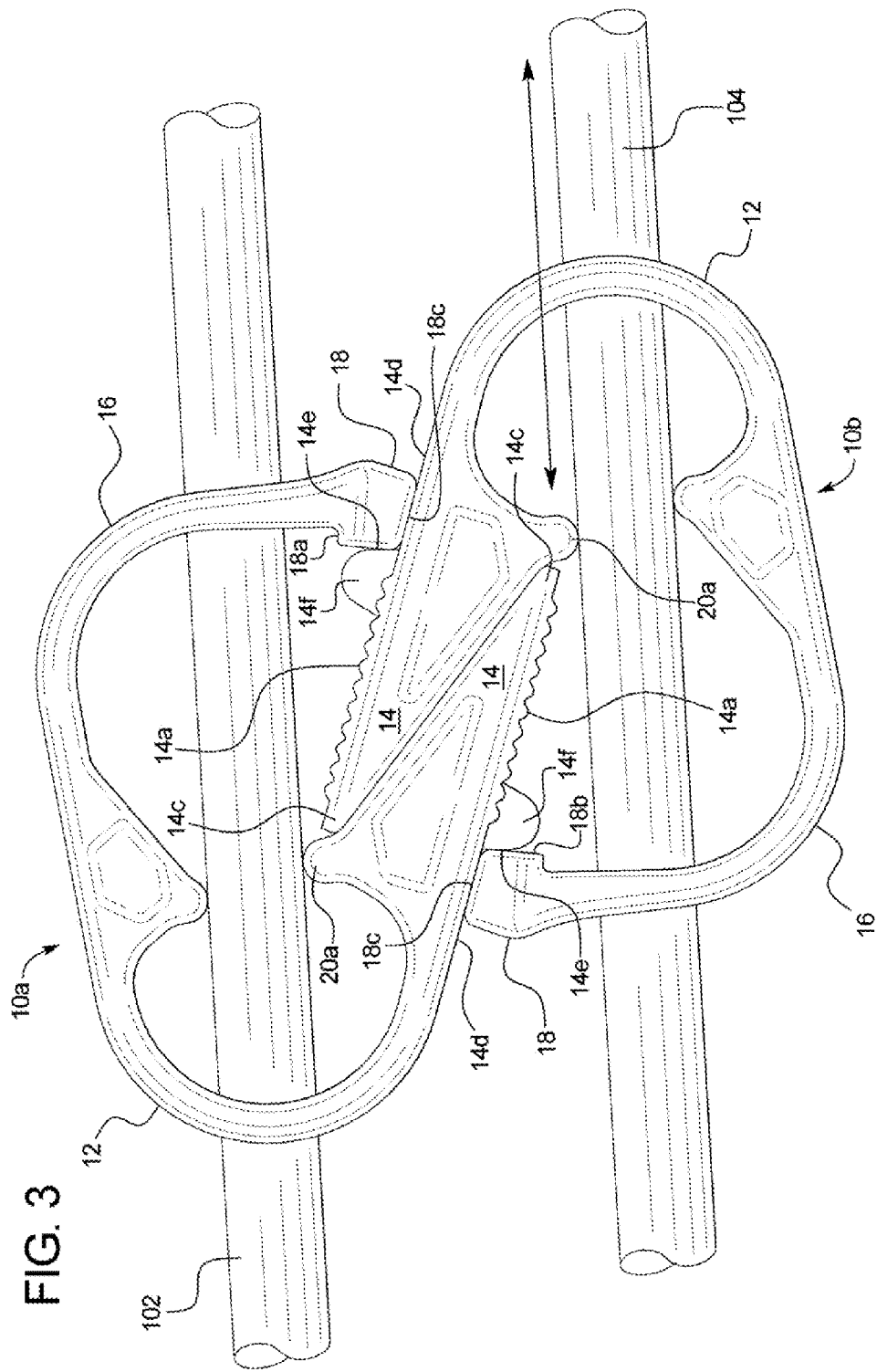
FIG. 3 is an elevation view of another embodiment of the interlocking tubing clamps of the present disclosure.

Referring now to FIGS. 2A and 2B to 5, various embodiments of clamps 10a and 10b (referred to herein collectively as clamps 10 or generally, individually as clamp 10) are illustrated. Clamps 10 are molded from a suitable material, such as polyethylene and in particular high density polyethylene ("HDPE", which has a desirable melting temperature and can be sterilized via gamma sterilization, steam sterilization and ethylene oxide ("EtO")), acetal, nylon, polypropylene, or nylon with glass. Each embodiment includes certain common features, such as, a tube holding portion 12, which defines an aperture (not seen) to allow a tube 102, 104 to extend through the tube holding portion as seen in FIGS. 1 and 3. Tube holding portion 12 extends in a cylindrical or semicircular manner in the illustrated embodiments, such that the aperture can be formed in the wall of the cylinder or semicircle.

A first arm 14 extends from one end of semicircular tube holding portion 12 and is generally straight, albeit having a triangular configuration. As arm 14 extends towards its distal end 14c, the first arm 14 as illustrated can be provided with ribs 14a on its outside surface for a user to contact clamp 10. Arm 14 is also provided with a triangular inner body 14b, which adds rigidity to first arm 14.

A second, curved arm 16 extends from the opposing end of semicircular tube holding portion 12. Curved arm 16 curves back towards first arm 14 and terminates at a catch 18 having an edge 18a extending inward towards tube holding portion 12. Edge 18a can be snap-fitted over distal tip 14c of first arm 14 to close clamps 10a and 10b after the interlocked clamps have been separated from each other. Curved arm 16, like tube holding portion 12, defines an aperture (not seen) in its wall to allow a tube 102, 104 to pass through clamp 10 as seen in FIGS. 1 and 3.

Located between U-shaped holding portion 12 and first arm 14 is a first clamping jaw 20a. Located between holding portion 12 and second arm 16 is a second clamping jaw 20b. Clamping jaws 20a and 20b are pressed towards each other when catch 18 is moved to snap-fit edge 18a over distal tip 14c of first arm 14 to close clamp 10. In the clamp closed position, clamping jaws 20a and 20b are spaced closely enough to each other to fully occlude tube 102, 104, but are also spaced far enough away from each other so as not to require an undue amount of force from the user to close clamp 10. To open clamp 10, the user can pull catch 18 outwards to allow the natural springiness of clamp 10 and the compressed tube 102, 104 to force arm 14 away from arm 16 to allow the tube to be opened for fluid flow.

FIGS. 2A and 2B illustrate one embodiment for configuring clamps 10a and 10b so that they may be interlocked together. Here, outer ribbed surface 14a of first arm 14 is angled or raised radially up (about distal end 14c) from straight outer surface 14d of first arm 14 to form an edge 14e, against which an inner wall 18b of the catch 18 of the mating clamp 10 is abutted. FIG. 2A shows arms 16 and catches 18 pulled away from straight outer surface 14d by about 4.5 mm, e.g., by a distance suitable to allow tubes 102, 104 to not be deformed when clamps 10a and 10b are imbricated. If whatever force is pulling second arms 16 outwardly in FIG. 2A is released, arms 16 will snap back towards the first arm 14 of the mating clamp 10, such that lower surfaces 18c of catches 18 will snap against straight outer surfaces 14d of arms 14 as seen in FIG. 2B. FIG. 2B illustrates that even in the imbricated or interlocked position, tubes 102 and 104 are not deformed in one preferred embodiment.

As illustrated in FIG. 2B, in one embodiment edge 14e is indented so as to form an upper lip that extends around edge 18a of catch 18 to help hold clamps 10a and 10b together in the interlocked position. Here, inner wall 18b of catch 18 abuts edge 14e of first arm 14. In FIG. 2B, if the user tries to pull clamps 10a and 10b axially apart (along the axes of tubes 102 and 104), inner wall 18b of catch 18 will abut against edge 14e of the mating clamp 10, precluding clamps 10a and 10b from being pulled apart unless enough force is applied to pull catches 18 up over edges 14e of the mating clamp 10.

As illustrated in FIGS. 2A and 2B, distal tips 14c of arms 14 imbed against clamping jaws 20a of the mating clamps 10, precluding the clamps 10a and 10b from being pushed axially together (along the axes of tubes 102 and 104). In essence, the embodiment of FIG. 2B locks raised ribbed surfaces 14a of clamps 10a and 10b between clamping jaws 20a and catches 18 of the mating clamp 10. The snap-fitted abutment of lower surface 18c of catch 18 to the straight outer surface 14d of the mating clamp 10 prevents clamps 10 from being compressed or closed any further. The user can pull curved arms 16 apart as is shown in FIG. 2A to unlock clamps 10a and 10b.

Referring now to FIG. 3, bumps or protrusions 14f, each having a contact side, surface or edge 14e, replace the raised ribbed surfaces 14d of the embodiment of FIGS. 2A and 2B. Otherwise, the embodiment of FIG. 3 operates very much the same as the embodiment of FIGS. 2A and 2B. In particular, lower surfaces 18c of catches 18 again snap against straight outer surfaces 14d of arms 14. Afterwards, if the user tries to pull clamps 10a and 10b axially apart (along the axes of tubes 102 and 104), inner wall 18b of catch 18 will abut against contact side, surface or edge 14e of the bump 14f of the mating clamp 10, precluding the clamps 10a and 10b from being pulled apart further unless enough force is applied to pull catches 18 up over edges 14e of the mating clamp 10. FIG. 3 also illustrates that even in the imbricated or interlocked position, tubes 102 and 104 are not deformed in one preferred embodiment.

Again, distal tips 14c of arms 14 imbed against clamping jaws 20a of the mating clamps 10, precluding the clamps 10a and 10b from being pushed axially together (along the axes of tubes 102 and 104). The embodiment of FIG. 3 locks ribbed surface 14a and protrusion 14f of clamp 10 between clamping jaw 20a and catch 18 of the mating clamp 10. The snap-fitted abutment of lower surface 18c of catch 18 to the straight outer surface 14d of the mating clamp 10 prevents clamps 10 from being compressed or closed any further. The user can again pull curved arms 16 apart to unlock clamps 10a and 10b.

Figure 4:
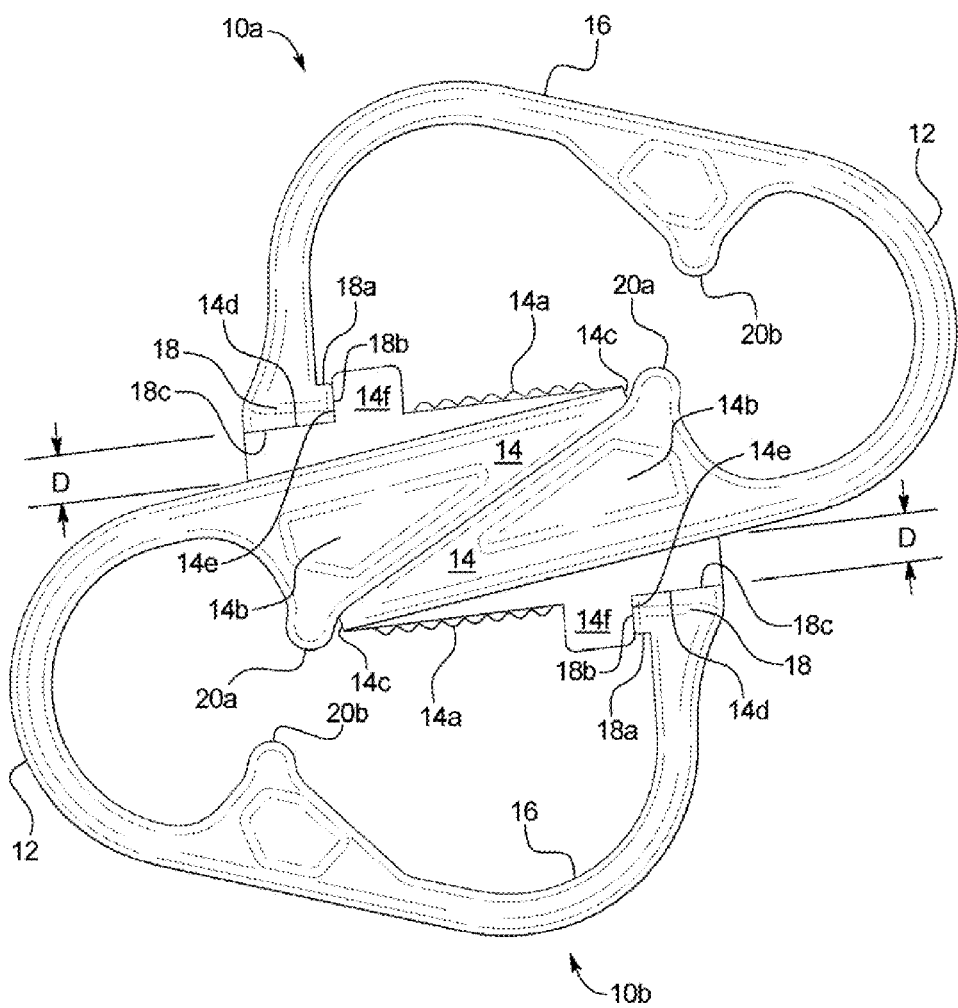
FIG. 4 is an elevation view of a further embodiment of the interlocking tubing clamps of the present disclosure.

Referring now to FIG. 4, bumps or protrusions 14f, each having a contact side, surface or edge 14e, are combined with an angularly or radially raised surfaces 14a. The embodiment of FIG. 4 operates very much the same as the embodiments of FIGS. 2A, 2B and 3. Again, lower surfaces 18c of catches 18 snap against raised outer surfaces 14d of arms 14. Afterwards, if the user tries to pull clamps 10a and 10b axially apart (along the axes of tubes 102 and 104), inner wall 18b of catch 18 will abut against contact side, surface or edge 14e of the bump 14f of the mating clamp 10, precluding the clamps 10a and 10b from being pulled apart further unless enough force is applied to pull catches 18 up over edges 14e of the mating clamp 10.

Again, distal tips 14c of arms 14 imbed against clamping jaws 20a of the mating clamps 10, precluding the clamps 10a and 10b from being pushed axially together (along the axes of tubes 102 and 104). The embodiment of FIG. 4 locks ribbed surface 14a and protrusion 14f of clamp 10 between clamping jaw 20a and catch 18 of the mating clamp 10. The snap-fitted abutment of lower surface 18c of catch 18 to the raised outer surface 14d of the mating clamp 10 prevents clamps 10 from being compressed or closed any further. The raised surfaces 14d also hold clamps 10a and 10b open by an extra distance D, which may be desirable to place even less compressive stress on tubes 102 and 104 during sterilization and prior to the opening of clamps 10a and 10b. The user can again pull curved arms 16 apart to unlock clamps 10a and 10b.

Figure 5:
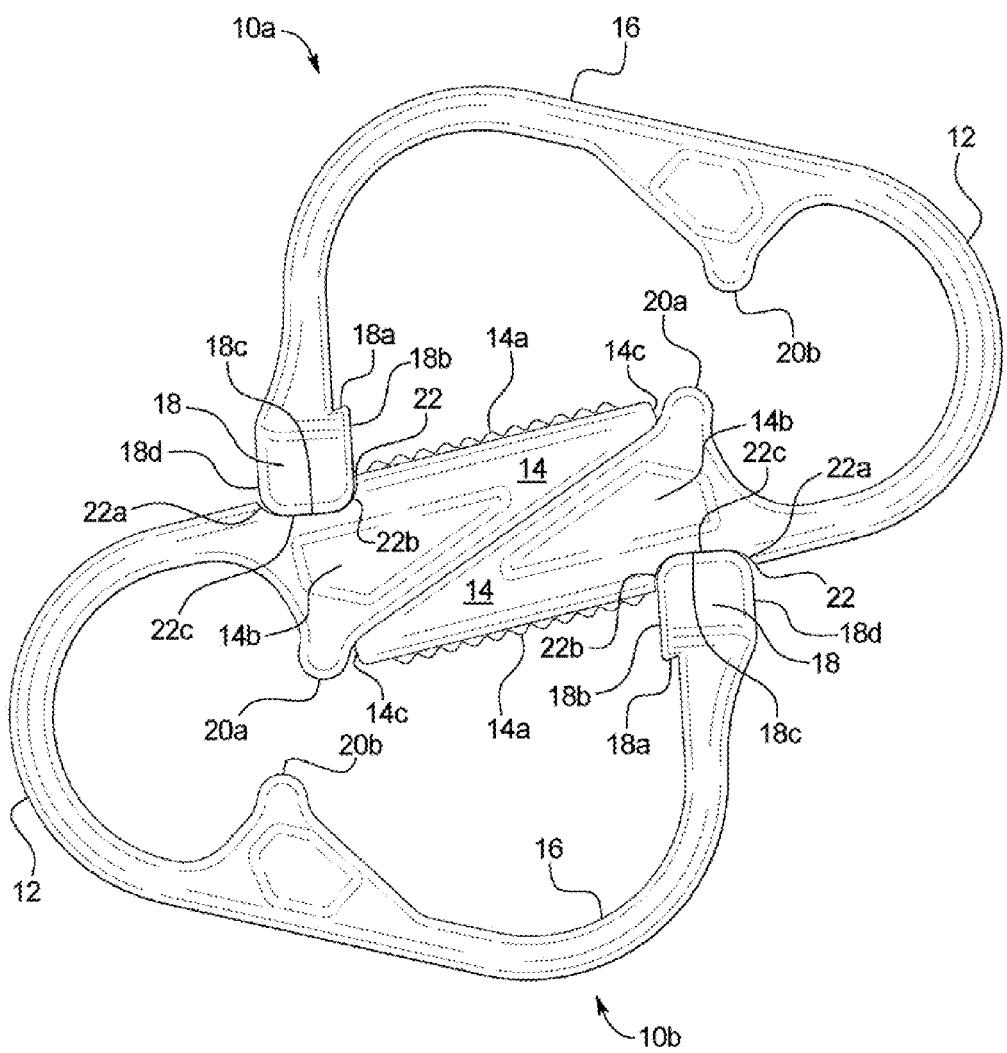
FIG. 5 is an elevation view of yet another embodiment of the interlocking tubing clamps of the present disclosure.

Referring now to FIG. 5, recesses 22 formed in first arms 14 replaces the raised ribbed surfaces 14a and bumps 14f of the previous embodiments. Recesses 22 each have a proximal edge or surface 22a, a distal edge or surface 22b and a bottom surface 22c. Proximal edges or surfaces 22a contact the outer sides or surfaces 18d of catches 18 to prevent clamps 10a and 10b from moving inwards towards each other along the axes of tubes 102 and 104. Distal edges or surfaces 22b contact the inner sides or surfaces 18b of catches 18 to prevent clamps 10a and 10b from being moved outwards with respect to each other along the axes of tubes 102 and 104. Bottom surfaces 22c of recesses 22 contact the lower sides or surfaces 18c of catches 18 to prevent clamps 10a and 10b from being compressed to occlude tubes 102 and 104. As before, the user can pull curved arms 16 apart to unlock clamps 10a and 10b from each other.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A tube clamp assembly comprising:
a first tube clamp including:
    a tube holding portion holding a tube, the tube holding portion of the first tube clamp including
        a first end and a second end,
    a first leg extending from and integral with the first end of the tube holding portion of the first tube clamp, and
    a second leg extending from and integral with the second end of the tube holding portion of the first tube clamp, the second leg defining a catch that is integral with the second leg of the first tube clamp,
    wherein the first leg is configured to be captured by the catch of the second leg of the first tube clamp to occlude the first tube;
a second tube clamp including
    a tube holding portion holding a second tube, the tube holding portion of the second tube clamp including a first end and a second end,
    a first leg extending from and integral with the first end of the tube holding portion of the second tube clamp, and
    a second leg extending from and integral with the second end of tube holding portion of the second tube clamp, the second leg defining a catch that is integral with the second leg of the second tube clamp,
    wherein the first leg of the second tube clamp is configured to be captured by the catch of of the second leg of the second tube clamp to occlude the second tube; and
wherein the first and second tube clamps are arranged such that (i) the catch of the second leg of the first tube clamp directly contacts and interlocks with the first leg of the second tube clamp and (ii) the catch of the second leg of the second tube clamp directly contacts and interlocks with the first leg of the first tube clamp to preclude the first tube clamp from occluding the first tube, and the second tube clamp from occluding the second tube.

2. The assembly of claim 1, wherein the first and second tube clamps are arranged such that the catch of the second leg of the first tube clamp directly contacts and interlocks with the first leg of the second tube clamp, and the catch of the second leg of the second tube clamp directly contacts and interlocks with the first leg of the first tube clamp to also preclude the first and second tube clamps from being moved towards and away from each other.

3. The assembly of claim 1, wherein the first leg of the first tube clamp and the first leg of the second tube clamp each include a locking feature located, respectively, at (i) an interface between the first leg of the first tube clamp and the tube holding portion of the first tube clamp and (ii) an interface between the first leg of the second tube clamp and a tube holding portion of the second tube clamp.

4. The assembly of claim 1, wherein the first leg of the second tube clamp and the first leg of the first tube clamp each include a raised edge against which the mated catch is abutted.

5. The assembly of claim 4, wherein the first and second tube clamps each include a tube clamping jaw that abuts distal ends of the first leg of the second tube clamp and the first leg of the first tube clamp, respectively, to interlock the first and second tube clamps together in cooperation with the raised edges.

6. The assembly of claim 1, wherein the first leg of the second tube clamp and the first leg of the first tube clamp each include a recess into which the mated catch is received.

\* \* \* \* \*